(12) United States Patent
Bergman

(10) Patent No.: US 10,745,493 B2
(45) Date of Patent: Aug. 18, 2020

(54) GRAFT COPOLYMER

(71) Applicant: Galderma S.A., Cham (CH)

(72) Inventor: Kristoffer Bergman, Stockholm (SE)

(73) Assignee: GALDERMA S.A., Cham (CH)

( * ) Notice: Subject to any disclaimer, the term of this patent is extended or adjusted under 35 U.S.C. 154(b) by 203 days.

(21) Appl. No.: 15/540,461

(22) PCT Filed: Dec. 29, 2015

(86) PCT No.: PCT/EP2015/081353
§ 371 (c)(1),
(2) Date: Jun. 28, 2017

(87) PCT Pub. No.: WO2016/107873
PCT Pub. Date: Jul. 7, 2016

(65) Prior Publication Data
US 2018/0002454 A1 Jan. 4, 2018

(30) Foreign Application Priority Data
Dec. 29, 2014 (EP) .................................. 14200376

(51) Int. Cl.
| C08B 37/08 | (2006.01) |
| C08B 37/02 | (2006.01) |
| C08B 37/00 | (2006.01) |
| C08G 81/00 | (2006.01) |
| A61K 8/91 | (2006.01) |
| A61K 8/73 | (2006.01) |
| A61Q 19/08 | (2006.01) |
| A61Q 19/00 | (2006.01) |
| A61L 27/20 | (2006.01) |

(52) U.S. Cl.
CPC ............ *C08B 37/0072* (2013.01); *A61K 8/73* (2013.01); *A61K 8/91* (2013.01); *A61L 27/20* (2013.01); *A61Q 19/00* (2013.01); *A61Q 19/08* (2013.01); *C08B 37/0021* (2013.01); *C08B 37/0069* (2013.01); *C08G 81/00* (2013.01); *A61K 2800/91* (2013.01)

(58) Field of Classification Search
CPC ............ C08B 37/0072; C08B 37/0069; C08B 37/0021; A61L 27/20
USPC .......................................................... 536/51
See application file for complete search history.

(56) References Cited

U.S. PATENT DOCUMENTS

| 6,630,457 | B1 * | 10/2003 | Aeschlimann ....... A61K 31/728 435/243 |
| 2003/0086899 | A1 * | 5/2003 | Jafari .................. A61K 9/0046 424/78.31 |
| 2006/0246137 | A1 | 11/2006 | Hermitte et al. |
| 2012/0276069 | A1 * | 11/2012 | Karperien ........ A61K 47/48784 424/93.7 |
| 2012/0301441 | A1 | 11/2012 | Karperien et al. |
| 2013/0052155 | A1 | 2/2013 | Marcolongo et al. |

FOREIGN PATENT DOCUMENTS

| CN | 1829743 A | 9/2006 |
| WO | WO 2011/059325 A2 | 5/2011 |

OTHER PUBLICATIONS

Lee, Y. E. et al. "Synthesis and characterization of novel crosslinked PEG-graft-chitosan/hyaluronic acid hydrogel" IEEE, 2007, pp. 251-252.
Wang, D. et al. "Multifunctional chondroitin sulphate for cartilage tissue—biomaterial integration" Nature materials, Nature Publishing Group, vol. 6, May 2007, pp. 385-392.
Weyers, A. et al. "Neoproteoglycans in tissue engineering" FEBS Journal 280, 2013, pp. 2511-2522, 2013 The Authors Journal compilation.
Shu, X. Z. et al. "Synthesis and evaluation of injectable, in situ crosslinkable synthetic extracellular matrices for tissue engineering" 2006 Wiley Periodicals, Inc., Journal of Biomedical Materials Research Part A, pp. 902-912.
Place, L. W. et al. "Synthesis and Characterization of Proteoglycan-Mimetic Graft Copolymers with Tunable Glycosaminoglycan Density" ACS Publications, Biomacromolecules, American Chemical Society, pp. A-I.
International Search Report (PCT/ISA/210) dated Mar. 10, 2016, by the European Patent Office as the International Searching Authority for International Application No. PCT/EP2015/081353.
Written Opinion (PCT/ISA/237) dated Mar. 10, 2016, by the European Patent Office as the International Searching Authority for International Application No. PCT/EP2015/081353.

* cited by examiner

*Primary Examiner* — Shaojia A Jiang
*Assistant Examiner* — Michael C Henry
(74) *Attorney, Agent, or Firm* — Foley & Lardner LLP; S. Talapatra

(57) ABSTRACT

A graft copolymer comprising: a core polymer comprising a crosslinked or non-crosslinked polysaccharide, a plurality of primary graft polymers covalently grafted to the core polymer, a plurality of secondary graft polymers covalently grafted to each primary graft polymer, an injectable dermal aesthetic formulation comprising such a graft copolymer and a method of preparing such a graft copolymer.

12 Claims, 1 Drawing Sheet

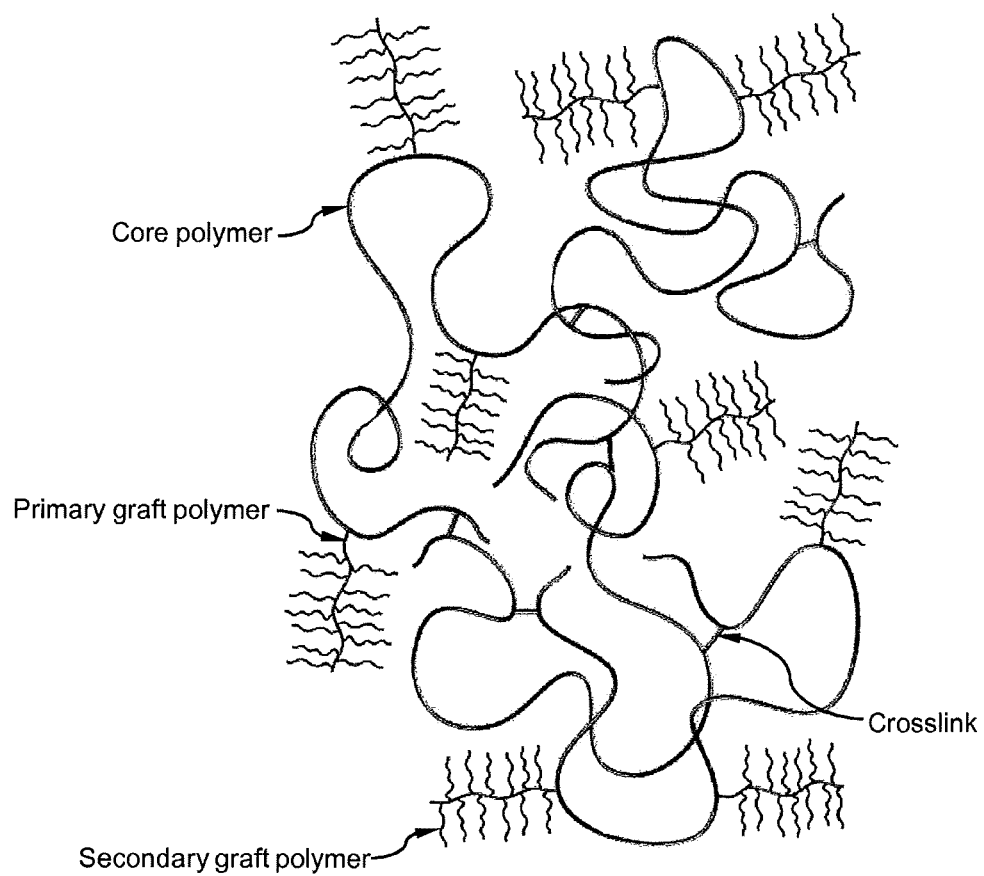

GRAFT COPOLYMER

FIELD OF THE INVENTION

The present invention relates to the field of copolymers comprising polysaccharides, formulations comprising such copolymers and the use of such copolymers and formulations in cosmetic and/or medical applications.

BACKGROUND

The mammalian extra cellular matrix (ECM) is composed of structural proteins and polysaccharides that provide support and regulate cellular activities. Although the exact composition of the ECM varies anatomically between different tissues, typical constituents include collagen fibers, elastin, laminin, fibronectin, proteoglycans and hyaluronan. Proteoglycans consist of sulfated glycosaminoglycans attached to a core protein and are considered to be responsible for a number physiological functions such as hydration of connective tissue, resistance towards compression and regulation of various cellular activities. Biomaterials for soft tissue applications such as devices for soft tissue augmentation, scaffolds for tissue engineering and vehicles for delivery of therapeutic agents are usually designed to mimic the natural ECM to achieve sufficient biocompatibility and blend in with the surrounding tissue so that the intended function is obtained (i.e. restore damaged tissue or release pharmaceuticals) without eliciting an unwanted host response. Hydrogels prepared from natural ECM components such as stabilized (crosslinked) hyaluronan possess many of the desired features and may be administered prior or post stabilization. Although crosslinking prolongs the duration of the degradable polymers that make up the network, it also alters the same polymers and their native properties may be lost. Hence, it is desired to maintain a low and efficient crosslinking. By combining multiple natural ECM components of various types these materials can be tailored to further resemble the ECM of the target site. Previously this has been done by forming mixed networks containing various crosslinked components (Shu et al. J Biomed Mater Res 79A: 902-912, 2006; Wang et al. Nat Mater 6: 385-392, 2007) or by creating proteoglycan mimicking constructs (Place et al. Biomacromolecules DOI: 10.102/bm501045k, 2014).

DESCRIPTION OF THE INVENTION

An object of the present disclosure is to provide graft copolymer compounds comprising different polymer and/or polysaccharide derivatives assembled in a controlled fashion. Graft copolymer compounds of the present disclosure may be used in injectable formulations which resemble the natural extra cellular matrix in terms of structural and/or physiochemical properties.

The present disclosure describes a new type of graft copolymer that may provide both physiochemical and structural resemblance to the natural ECM by containing a high content of native ECM components that are modified to a low degree. The graft copolymers may be assembled through a modular synthetic approach.

According to a first aspect illustrated herein, there is provided a graft copolymer comprising:
a core polymer comprising a crosslinked or non-crosslinked polysaccharide,
a plurality of primary graft polymers covalently grafted to the core polymer, and
a plurality of secondary graft polymers covalently grafted to each primary graft polymer.

The graft copolymer of the present disclosure may also be seen as a macromolecular structure, comprised of two types of substructures.

The first substructure (core polymer) comprises a crosslinked or non-crosslinked polysaccharide, preferably selected from the group consisting of crosslinked or non-crosslinked, sulfated or non-sulfated glycosaminoglycans such as hyaluronan, chondroitin sulphate, heparan sulphate, heparosan, heparin, dermatan sulphate and keratan sulphate. Typically, the molecular weight of the polysaccharide of the core polymer, in its native or uncrosslinked state, is in the range of 50-5000 kDa, preferably in the range of 100-1000 kDa.

The second substructure comprises multiple polymer chains (secondary graft polymers), preferably polysaccharide chains, each attached (grafted) by their respective terminal reducing end onto a polymer chain (primary graft polymer) that in turn is attached (grafted) onto the first substructure (core polymer).

The polysaccharide chains of the secondary graft polymers may or may not be of the same type and are also preferably selected from the group consisting of sulfated and non-sulfated glycosaminoglycans, such as hyaluronan, chondroitin sulphate, heparan sulphate, heparosan, heparin, dermatan sulphate and keratan sulphate. Typically, the molecular weight of the polysaccharide chains of the secondary graft polymers is in the range of 10-1000 kDa, preferably in the range of 20-500 kDa.

The primary graft polymer may be any water soluble polymer. The primary graft polymer is typically selected from the group consisting of water soluble polysaccharides. In a preferred embodiment, the primary graft polymer is dextran. The molecular weight of the primary graft polymer is preferably in the range of 1-1000 kDa.

The primary graft polymers and the core polymer are preferably covalently connected to each other, either by a direct covalent bond between the two molecules, or by a linking group covalently bonded to both the primary graft polymer and the core polymer.

The secondary graft polymers and the primary graft polymer are preferably covalently connected to each other, either by a direct covalent bond between the two molecules, or by a linking group covalently bonded to both the secondary graft polymer and the primary graft polymer.

The core polymer, primary graft polymer and secondary graft polymer are preferably different polymers. Preferably at least two of the core polymer, primary graft polymer and secondary graft polymer are different polymers. More preferably all three of the core polymer, primary graft polymer and secondary graft polymer are different polymers.

In some embodiments the core polymer comprises a polysaccharide selected from the group consisting of sulfated and non-sulfated glycosaminoglycans.

In some embodiments the core polymer comprises a polysaccharide selected from the group consisting of hyaluronic acid, hyaluronan, chondroitin sulphate, heparan sulphate, heparosan, heparin, dermatan sulphate and keratan sulphate, or a combination thereof.

In some embodiments the core polymer, in its native or uncrosslinked state, has a molecular weight in the range of 50-5000 kDa, preferably in the range of 100-1000 kDa.

In some embodiments the core polymer is crosslinked.

In some embodiments core polymer is crosslinked by ether bonds.

In some embodiments the core polymer is crosslinked by 1,4-Butanediol diglycidyl ether (BDDE).

In some embodiments the core polymer comprises a polysaccharide gel.

One of the most widely used biocompatible polymers for medical use is hyaluronic acid (HA). HA is a naturally occurring polysaccharide belonging to the group of glycosaminoglycans (GAGs). Hyaluronic acid and the other GAGs are negatively charged heteropolysaccharide chains which have a capacity to absorb large amounts of water. Hyaluronic acid and products derived from hyaluronic acid are widely used in the biomedical and cosmetic fields, for instance during viscosurgery and as a dermal filler.

Water-absorbing gels, or hydrogels, are widely used in the biomedical field. They are generally prepared by chemical crosslinking of polymers to infinite networks. While native hyaluronic acid and certain crosslinked hyaluronic acid products absorb water until they are completely dissolved, crosslinked hyaluronic acid gels typically absorb a certain amount of water until they are saturated, i.e. they have a finite liquid retention capacity, or swelling degree.

Since hyaluronic acid is present with identical chemical structure except for its molecular mass in most living organisms, it gives a minimum of foreign body reactions and allows for advanced medical uses. Crosslinking and/or other modifications of the hyaluronic acid molecule is typically necessary to improve its duration in vivo. Furthermore, such modifications affect the liquid retention capacity of the hyaluronic acid molecule. As a consequence thereof, hyaluronic acid has been the subject of many modification attempts.

In some embodiments the core polymer comprises a hyaluronic acid.

The hyaluronic acid may be a modified, e.g. branched or crosslinked, hyaluronic acid. According to certain embodiments the hyaluronic acid is a crosslinked hyaluronic acid. According to specific embodiments the hyaluronic acid is a hyaluronic acid gel.

Unless otherwise provided, the term "hyaluronic acid" encompasses all variants and combinations of variants of hyaluronic acid, hyaluronate or hyaluronan, of various chain lengths and charge states, as well as with various chemical modifications, including crosslinking. That is, the term also encompasses the various hyaluronate salts of hyaluronic acid with various counter ions, such as sodium hyaluronate. Various modifications of the hyaluronic acid are also encompassed by the term, such as oxidation, e.g. oxidation of —$CH_2OH$ groups to —CHO and/or —COOH; periodate oxidation of vicinal hydroxyl groups, optionally followed by reduction, e.g. reduction of —CHO to —$CH_2OH$ or coupling with amines to form imines followed by reduction to secondary amines; sulphation; deamidation, optionally followed by deamination or amide formation with new acids; esterification; crosslinking; substitutions with various compounds, e.g. using a crosslinking agent or a carbodiimide assisted coupling; including coupling of different molecules, such as proteins, peptides and active drug components, to hyaluronic acid; and deacetylation. Other examples of modifications are isourea, hydrazide, bromocyan, monoepoxide and monosulfone couplings.

The hyaluronic acid can be obtained from various sources of animal and non-animal origin. Sources of non-animal origin include yeast and preferably bacteria. The molecular weight of a single hyaluronic acid molecule is typically in the range of 0.1-10 MDa, but other molecular weights are possible.

In certain embodiments the concentration of said hyaluronic acid is in the range of 1 to 100 mg/ml. In some embodiments the concentration of said hyaluronic acid is in the range of 2 to 50 mg/ml. In specific embodiments the concentration of said hyaluronic acid is in the range of 5 to 30 mg/ml or in the range of 10 to 30 mg/ml. In certain embodiments, the hyaluronic acid is crosslinked. Crosslinked hyaluronic acid comprises crosslinks between the hyaluronic acid chains, which creates a continuous network of hyaluronic acid molecules which is held together by the covalent crosslinks, physical entangling of the hyaluronic acid chains and various interactions, such as electrostatic interactions, hydrogen bonding and van der Waals forces.

Crosslinking of the hyaluronic acid may be achieved by modification with a chemical crosslinking agent. The chemical crosslinking agent may for example selected from the group consisting of divinyl sulfone, multiepoxides and diepoxides. According to an embodiment, the hyaluronic acid is crosslinked by a bi- or polyfunctional crosslinking agent comprising two or more glycidyl ether functional groups. According to embodiments the chemical crosslinking agent is selected from the group consisting of 1,4-butanediol diglycidyl ether (BDDE), 1,2-ethanediol diglycidyl ether (EDDE) and diepoxyoctane. According to a preferred embodiment, the chemical crosslinking agent is 1,4-butanediol diglycidyl ether (BDDE).

As mentioned, crosslinking of hyaluronic acid to form the crosslinked hyaluronic acid gel may for example be achieved by modification with a chemical crosslinking agent, for example BDDE (1,4-butandiol diglycidylether). The hyaluronic acid concentration and the extent of crosslinking affects the mechanical properties, e.g. the elastic modulus G', and stability properties of the gel. Crosslinked hyaluronic acid gels are often characterized in terms of "degree of modification". The degree of modification of hyaluronic acid gels generally range between 0.1 and 15 mole %. The degree of modification (mole %) describes the amount of crosslinking agent(s) that is bound to HA, i.e. molar amount of bound crosslinking agent(s) relative to the total molar amount of repeating HA disaccharide units. The degree of modification reflects to what degree the HA has been chemically modified by the crosslinking agent. Reaction conditions for crosslinking and suitable analytical techniques for determining the degree of modification are all well known to the person skilled in the art, who easily can adjust these and other relevant factors and thereby provide suitable conditions to obtain a degree of modification in the range of 0.1-2% and verify the resulting product characteristics with respect to the degree of modification. A BDDE (1,4-butandiol diglycidylether) crosslinked hyaluronic acid gel may for example be prepared according to the method described in Examples 1 and 2 of published international patent application WO 9704012.

In some embodiments of the graft copolymer, the core polymer is a hyaluronic acid gel crosslinked by a chemical crosslinking agent, wherein the concentration of said hyaluronic acid is in the range of 10 to 30 mg/ml and the degree of modification with said chemical crosslinking agent is in the range of 0.1 to 2 mole %.

Hyaluronic acid gels may also comprise a portion of hyaluronic acid which is not crosslinked, i.e not bound to the three-dimensional crosslinked hyaluronic acid network. However, it is preferred that at least 50% by weight, preferably at least 60% by weight, more preferably at least 70% by weight, and most preferably at least 80% by weight, of the hyaluronic acid in a gel composition form part of the crosslinked hyaluronic acid network.

In some embodiments the primary graft polymers comprise a water soluble polymer. In some embodiments the primary graft polymers comprise a water soluble polysaccharide. In some embodiments the primary graft polymers are dextran.

In some embodiments the primary graft polymers have a molecular weight in the range of 1-1000 kDa.

In some embodiments the primary graft polymers are covalently grafted to the core polymer by single end-point attachment.

In some embodiments the primary graft polymers are covalently grafted directly to the core polymer. Direct covalent bonding of the primary graft polymers to the core polymer may be accomplished by a coupling agent, e.g. DMTMM, which may facilitate covalent bond formation without becoming part of the linkage.

In some embodiments the primary graft polymers are covalently grafted to the core polymer through a linking group. A linking group may be any moiety that can have a covalent bond to both the primary graft polymers and the core polymer. For example, a linking group may form an ester, ether, amine or amide bond both the primary graft polymers and the core polymer. A linking group may be formed by reacting a linking agent with both the primary graft polymers and the core polymer. The linking group may be for example be butanediol diglycidyl ether, or hexamethylenediamine.

In some embodiments, and the primary graft polymer further has:
A) A back-bone that carries a plurality of (at least two) homofunctional pendant groups capable of creating a covalent linkage with the reducing end of a polysaccharide. These functional groups can either be present on the polymer in its native form, or they can be introduced prior to linking with the secondary graft polymers, optionally via a spacer.
B) The capability of forming a single-point covalent linkage to the first substructure (core polymer). This capability may either be present in the primary graft polymer in its native form, or it can be introduced prior coupling to the core polymer using, for instance, a linker. The single-point covalent linkage to the core polymer may preferably be formed after crosslinking of the core polymer but before grafting of the secondary graft polymers to the primary graft polymer.

In some embodiments the secondary graft polymers are selected from the group consisting of sulfated and non-sulfated glycosaminoglycans, or a combination thereof.

In some embodiments the secondary graft polymers are selected from the group consisting of hyaluronan, hyaluronic acid, chondroitin sulphate, heparan sulphate, heparosan, heparin, dermatan sulphate and keratan sulphate, or a combination thereof.

In some embodiments the secondary graft polymers are chondroitin sulphate.

In some embodiments the secondary graft polymers have a molecular weight in the range of 10-1000 kDa. In some embodiments the secondary graft polymers have a molecular weight in the range of 20-500 kDa.

In some embodiments the secondary graft polymers are covalently grafted to the primary graft polymers by single end-point attachment.

In some embodiments the secondary graft polymers are covalently grafted directly to the primary graft polymers. Direct covalent bonding of the secondary graft polymers to the primary graft polymers may be accomplished by a coupling agent, e.g. DMTMM, which may facilitate covalent bond formation without becoming part of the linkage.

In some embodiments the secondary graft polymers are covalently grafted to the primary graft polymers through a linking group. A linking group may be any moiety that can have a covalent bond to both the secondary graft polymers and the primary graft polymers. For example, a linking group may form an ester, ether, amine or amide bond both the primary graft polymers and the core polymer. A linking group may be formed by reacting a linking agent with both the secondary graft polymers and the primary graft polymers.

The linking group may be for example be a diol, a diglycidyl ether, or a diamine. In an embodiment the linking group is a diamine, preferably hexamethylenediamine or diaminooxy-propane (O,O'-(propane-1,3-diyl)bis(hydroxylamine)).

The linking group may be for example be butanediol diglycidyl ether, or hexamethylenediamine.

In some embodiments of the graft copolymer, the core polymer is a crosslinked hyaluronic acid, the primary graft polymers are dextran and the secondary graft polymers are chondroitin sulphate.

The graft copolymer is preferably biocompatible. This implies that no, or only very mild, immune response occurs when the graft copolymer is introduced into the tissue of an individual. That is, no or only very mild undesirable local or systemic effects occur in the treated individual.

The graft copolymers of the present disclosure may for example be used in injectable formulations for treatment of soft tissue disorders, including but not limited to, corrective and aesthetic treatments.

The graft copolymers of the present disclosure may for example be used in injectable formulations for cosmetic surgery, e.g. dermal filling, body contouring and facial contouring, in medical surgery, e.g. dermal filling, body contouring, prevention of tissue adhesion, formation of channels, incontinence treatment, and orthopaedic applications, and for hydrating and/or revitalizing the skin.

According to a second aspect illustrated herein, there is provided an injectable aesthetic formulation comprising a graft copolymer as described herein with reference to the first aspect.

According to a third aspect illustrated herein, there is provided an injectable pharmaceutical formulation comprising a graft copolymer as described herein with reference to the first aspect.

The graft copolymers of the present disclosure may also be used in injectable formulations for the transport or administration and slow or controlled release of various pharmaceutical or cosmetic substances.

The injectable pharmaceutical formulation may optionally include one or more other pharmaceutically acceptable components, including, but not limited to, buffers, preservatives, tonicity adjusters, salts, antioxidants, osmolality adjusting agents, emulsifying agents, wetting agents, sweetening or flavoring agents, and the like.

The injectable pharmaceutical formulation may optionally include a pharmaceutically effective amount of an anesthetic agent. The anesthetic agent may be a local anesthetic agent, e.g. an aminoamide local anesthetic or aminoester local anesthetic. Examples of anesthetic agents include, but are not limited to, lidocaine, ambucaine, amolanone, amylocaine, benoxinate, benzocaine, betoxycaine, biphenamine, bupivacaine, butacaine, butamben, butanilicaine, butethamine, butoxycaine, carticaine, chloroprocaine, cocaethylene, cyclomethycaine, dibucaine, dimethisoquin, dimethocaine, diperodon, dicyclomine, ecgonidine, ecgonine, ethyl chloride, etidocaine, β-eucaine, euprocin, fenalcomine, formocaine, hexylcaine, hydroxytetracaine, isobutyl p-aminobenzoate, leucinocaine mesylate, levoxadrol, lidocaine, mepivacaine, meprylcaine, metabutoxycaine, methyl chloride, myrtecaine, naepaine, octacaine, orthocaine, oxethazaine, parethoxycaine, phenacaine, phenol, piperocaine, piridocaine, polidocanol, pramoxine, prilocaine, procaine, propanocaine, proparacaine, propipocaine, propoxycaine, pseudococaine, pyrrocaine, ropivacaine, salicyl alcohol, tetracaine, tolycaine, trimecaine, zolamine, combinations thereof, and salts thereof. Examples of aminoester local anesthetics include, but are not limited to procaine, chloroprocaine, cocaine, cyclomethycaine, dimethocaine (larocaine), propoxycaine, procaine (novocaine), proparacaine, tetracaine (amethocaine). Non-limiting examples of aminoamide local anesthetics include articaine, bupivacaine, cinchocaine (dibucaine), etidocaine, levobupivacaine, lidocaine (lignocaine), mepivacaine, piperocaine, prilocaine, ropivacaine, trimecaine, or a combination thereof.

According to a fourth aspect illustrated herein, there is provided a method of preparing a graft copolymer comprising the steps:
a) providing a core polymer comprising a crosslinked or non-crosslinked polysaccharide comprising a plurality of pendant functional groups,
b) providing a primary graft polymer comprising a terminal functional group and a plurality of pendant functional groups,
c) providing a secondary graft polymer comprising a terminal functional group,
d) mixing the core polymer with the primary graft polymer under conditions allowing covalent binding of the primary graft polymer exclusively to the pendant functional groups of the core polymer via the terminal functional group of the primary graft polymer,
e) mixing the grafted product of step d) with the secondary graft polymer under conditions allowing covalent binding of the secondary graft polymer exclusively to the pendant functional groups of the primary graft polymer via the terminal functional group of the secondary graft polymer.

By "terminal functional group" is meant a functional group present on a terminal (end) monomer residue, of the polymer. By "pendant functional group" is meant a functional group present on a monomer residue of the polymer, which is not a terminal monomer residue.

The term "exclusively", as used herein in steps d) and e) of the method should be understood as meaning that a majority of the covalent bonds that are formed are of the intended type, i.e. covalent binding of the secondary graft polymer exclusively to the pendant functional groups of the primary graft polymer via the terminal functional group of the secondary graft polymer, and covalent binding of the secondary graft polymer exclusively to the pendant functional groups of the primary graft polymer via the terminal functional group of the secondary graft polymer, respectively. Preferably at least 90%, more preferably at least 95%, of the covalent bonds that are formed are of the intended type.

In some embodiments, the pendant groups of the primary graft polymer in step b) are selected so as not to bind to the core polymer or other primary graft polymers under the conditions used in step d).

In some embodiments, the pendant groups of the secondary graft polymer in step c) are selected so as not to bind to the core polymer, secondary graft polymer or other primary graft polymers under the conditions used in step e).

In, some embodiments, the pendant groups of the primary graft polymer in step b) are provided with protecting groups.

In some embodiments, the pendant groups of the secondary graft polymer in step c) are provided with protecting groups.

In some embodiments, the terminal group of the primary graft polymer in step b) is provided with a reactive linking group.

In some embodiments, the terminal group of the secondary graft polymer in step c) is provided with a reactive linking group.

The core polymer may be a crosslinked or non-crosslinked polysaccharide. A crosslinked core polymer is typically prepared by crosslinking using known methods, including but not limited to, methods that result in the formation of ether, ester, amide, hydrazone bonds and analogues, and any combination thereof. The reducing end of the core polymer may further be converted to an alcohol using, for instance, sodium borohydride. The degree of crosslinking is typically in the range of 0-50%, preferably in the range of 0.5-10%, based on the number of repeating units that are involved in a crosslink.

The graft copolymer is typically prepared by first coupling the primary graft polymers to the core polymer and before linking with the secondary grafts. If required, the backbone of the primary grafts may be derivatized to carry multiple homofunctional substituent groups suitable for creating a linkage with the reducing end of the secondary grafts. Such homofunctional substituent groups may for example be selected from the group consisting of nucleophiles, such as primary amines, hydrazides, carbazates, semi-carbazides, thiosemicarbazides, thiocarbazates or aminooxy, and they may be attached to the back-bone of the primary graft polymer using a spacer.

Preferably, the core polymer and the secondary graft polymer are devoid of the chosen functional groups on the primary graft polymers to avoid competing reactions. In some embodiments, the reactivity of the functional groups on the primary graft polymers is instead temporarily shielded using a protecting group, which is removed prior linking with the polysaccharide side-chains (secondary grafts).

In some embodiments, the primary graft polymer is linked to 0.1-100%, preferably to 0.5-50% or 1-25%, of the repeating units of the core polymer. The primary graft polymer may be linked to the core polymer using a linker, preferably selected from the group consisting of homobifunctional primary amines, hydrazides, carbazates, semi-carbazides, thiosemicarbazides, thiocarbazates or aminooxy or any combination thereof, including combinations of heterobifunctional versions of the same, more preferably a homobifunctional primary amine. The coupling may for example be carried out by 1) attaching one end of the bifunctional linker to the native primary graft polymer by, for instance, reductive amination in the presence of a reducing agent, such as sodium cyanoborohydride, and 2) attaching the other end to the carboxyl groups of the first substructure by, for instance, amide bond formation using a suitable coupling agent (e.g. carbodiimides together with activator such as a hydroxylamine derivative, or a triazine). Preferably, only one linker is attached to each chain of the primary graft polymer (in step 1), however, a significant excess of the bifunctional linker is preferably used in the in the process to avoid creating a linkage in both ends of the linker.

After linking of the primary graft polymers to the core polymer, the secondary graft polymers are attached to the primary graft polymers, for example by ligation with 1-100%, preferably to 5-75%, more preferably 10-50% (provided the total number of secondary grafts on each primary graft polymer in average is greater than 2) of the functional substituent groups on the primary graft polymers. If necessary, the step is carried out after deprotection in such case that the functional groups on the primary grafts have been temporarily shielded by a protecting group.

The terms "linker", "spacer", and "linking group" are use interchangeably herein to denote a bifunctional moiety forming a covalent bond with to both the primary graft polymers and the core polymer or with both the primary graft polymers and the secondary graft polymers. In an embodiment the linking group is a diamine, preferably hexamethylenediamine or diaminooxy-propane (O,O'-(propane-1,3-diyl)bis(hydroxylamine)).

According to further aspects illustrated herein, there is provided a graft copolymer, or injectable pharmaceutical formulation comprising a graft copolymer, as described herein, for use as a medicament. The copolymer or formulation may be useful, for example in the treatment of various dermatological conditions.

According to further aspects illustrated herein, there is provided a method of cosmetically treating skin, which comprises administering to the skin an injectable formulation comprising the graft copolymer as described herein. In certain embodiments the injectable formulation is injected into the cutis and/or subcutis.

According to further aspects illustrated herein, there is provided the use of an injectable formulation as described above for cosmetic, non-medical, treatment of a subject by injection of the formulation into the skin of the subject. A purpose of the cosmetic, non-medical, treatment may be for improving the appearance of the skin, filling wrinkles or contouring the face or body of a subject. The cosmetic, nonmedical, use does not involve treatment of any form of disease or medical condition.

According to certain embodiments, there is provided the use of an injectable formulation as described above for improving the appearance of skin, filling wrinkles or contouring the face or body of a subject. The use preferably comprises injecting the formulation into the cutis and/or subcutis of a human subject. According to certain embodiments, there is provided the use of the injectable formulation as described above for filling wrinkles or contouring the face or body of a subject. According to certain embodiments, there is provided the use of the injectable formulation as described above for skin revitalization.

The use of the injectable formulation for improving the appearance of skin, filling wrinkles or contouring the face or body of a subject, may be essentially or totally nonmedical, e.g. purely cosmetic.

The term "molecular weight" as used herein in connection with various polymers, e.g. polysaccharides, refers to the weight average molecular weight, $M_w$, of the polymers, which is well defined in the scientific literature.

The weight average molecular weight can be determined by, e.g., static light scattering, small angle neutron scattering, X-ray scattering, and sedimentation velocity. The unit of the molecular weight is Da or g/mol.

The person skilled in the art realizes that the present invention is by no means limited to the preferred embodiments described herein. On the contrary, many modifications and variations are possible within the scope of the appended claims. Additionally, variations to the disclosed embodiments can be understood and effected by the skilled person in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage.

Itemized Listing of Embodiments

The following is a non-limiting and itemized listing of embodiments of the present disclosure, presented for the purpose of describing various features and combinations provided by the invention in certain of its aspects.

1. A graft copolymer comprising:
a core polymer comprising a crosslinked or non-crosslinked polysaccharide,
a plurality of primary graft polymers covalently grafted to the core polymer,
a plurality of secondary graft polymers covalently grafted to each primary graft polymer.
2. A graft copolymer according to item 1, wherein the core polymer comprises a polysaccharide selected from the group consisting of sulfated and non-sulfated glycosaminoglycans.
3. A graft copolymer according to any one of the previous items, wherein the core polymer comprises a polysaccharide selected from the group consisting of hyaluronic acid, hyaluronan, chondroitin sulphate, heparan sulphate, heparosan, heparin, dermatan sulphate and keratan sulphate, or a combination thereof.
4. A graft copolymer according to any one of the previous items, wherein the core polymer comprises hyaluronic acid.
5. A graft copolymer according to any one of the previous items, wherein the core polymer has a molecular weight in the range of 50-5000 kDa.
6. A graft copolymer according to any one of the previous items, wherein the core polymer has a molecular weight in the range of 100-1000 kDa.
7. A graft copolymer according to any one of the previous items, wherein the core polymer is crosslinked.
8. A graft copolymer according to any one of the previous items, wherein the core polymer is crosslinked by ether bonds.
9. A graft copolymer according to any one of the previous items, wherein the core polymer is crosslinked by 1,4-Butanediol diglycidyl ether (BDDE).
10. A graft copolymer according to any one of the previous items, wherein the core polymer comprises polysaccharide gel.
11. A graft copolymer according to any one of the previous items, wherein the primary graft polymers comprise a water soluble polymer.
12. A graft copolymer according to any one of the previous items, wherein the primary graft polymers comprise a water soluble polysaccharide.
13. A graft copolymer according to any one of the previous items, wherein the primary graft polymers are dextran.
14. A graft copolymer according to any one of the previous items, wherein the primary graft polymers have a molecular weight in the range of 1-1000 kDa.
15. A graft copolymer according to any one of the previous items, wherein the secondary graft polymers are selected from the group consisting of sulfated and non-sulfated glycosaminoglycans, or a combination thereof.

16. A graft copolymer according to any one of the previous items, wherein the secondary graft polymers are selected from the group consisting of hyaluronan, hyaluronic acid, chondroitin sulphate, heparan sulphate, heparosan, heparin, dermatan sulphate and keratan sulphate, or a combination thereof.

17. A graft copolymer according to any one of the previous items, wherein the secondary graft polymers are chondroitin sulphate.

18. A graft copolymer according to any one of the previous items, wherein the secondary graft polymers have a molecular weight in the range of 10-1000 kDa.

19. A graft copolymer according to any one of the previous items, wherein the secondary graft polymers have a molecular weight in the range of 20-500 kDa.

20. A graft copolymer according to any one of the previous items, wherein the primary graft polymers are covalently grafted to the core polymer by single end-point attachment.

21. A graft copolymer according to any one of the previous items, wherein the primary graft polymers are covalently grafted directly to the core polymer.

22. A graft copolymer according to any one of the previous items, wherein the primary graft polymers are covalently grafted to the core polymer through a linking group.

23. A graft copolymer according to any one of the previous items, wherein the secondary graft polymers are covalently grafted to the primary graft polymers by single end-point attachment.

24. A graft copolymer according to any one of the previous items, wherein the secondary graft polymers are covalently grafted directly to the primary graft polymers.

25. A graft copolymer according to any one of the previous items, wherein the secondary graft polymers are covalently grafted to the primary graft polymers through a linking group.

26. A graft copolymer according to any one of the previous items, wherein the core polymer is a crosslinked hyaluronic acid, the primary graft polymers are dextran and the secondary graft polymers are chondroitin sulphate.

27. An injectable dermal aesthetic formulation comprising a graft copolymer according to any one of items 1-26.

28. An injectable pharmaceutical formulation comprising a graft copolymer according to any one of items 1-26.

29. A graft copolymer according to any one of items 1-26 for use as a medicament.

30. A method of preparing a graft copolymer comprising the steps:
a) providing a core polymer comprising a crosslinked or non-crosslinked polysaccharide comprising a plurality of pendant functional groups,
b) providing a primary graft polymer comprising a terminal functional group and a plurality of pendant functional groups,
c) providing a secondary graft polymer comprising a terminal functional group,
d) mixing the core polymer with the primary graft polymer under conditions allowing covalent binding of the primary graft polymer exclusively to the pendant functional groups of the core polymer via the terminal functional group of the primary graft polymer,
e) mixing the grafted product of step d) with the secondary graft polymer under conditions allowing covalent binding of the secondary graft polymer exclusively to the pendant functional groups of the primary graft polymer via the terminal functional group of the secondary graft polymer.

31. A method according to item 30, wherein the core polymer comprises a polysaccharide selected from the group consisting of sulfated and non-sulfated glycosaminoglycans.

32. A method according to any one of items 30-31, wherein the core polymer comprises a polysaccharide selected from the group consisting of hyaluronic acid, hyaluronan, chondroitin sulphate, heparan sulphate, heparosan, heparin, dermatan sulphate and keratan sulphate, or a combination thereof.

33. A method according to any one of items 30-32, wherein the core polymer comprises hyaluronic acid.

34. A method according to any one of items 30-33, wherein the core polymer has a molecular weight in the range of 50-5000 kDa.

35. A method according to any one of items 30-34, wherein the core polymer has a molecular weight in the range of 100-1000 kDa.

36. A method according to any one of items 30-35, wherein the core polymer is crosslinked.

37. A method according to any one of items 30-36, wherein the core polymer is crosslinked by ether bonds.

38. A method according to any one of items 30-37, wherein the core polymer is crosslinked by 1,4-Butanediol diglycidyl ether (BDDE).

39. A method according to any one of items 30-38, wherein the core polymer comprises polysaccharide gel.

40. A method according to any one of items 30-39, wherein the primary graft polymers comprise a water soluble polymer.

41. A method according to any one of items 30-40, wherein the primary graft polymers comprise a water soluble polymer polysaccharide.

42. A method according to any one of items 30-41, wherein the primary graft polymers are dextran.

43. A method according to any one of items 30-42, wherein the primary graft polymers have a molecular weight in the range of 1-1000 kDa.

44. A method according to any one of items 30-43, wherein the secondary graft polymers are selected from the group consisting of sulfated and non-sulfated glycosaminoglycans, or a combination thereof.

45. A method according to any one of items 30-44, wherein the secondary graft polymers are selected from the group consisting of hyaluronan, hyaluronic acid, chondroitin sulphate, heparan sulphate, heparosan, heparin, dermatan sulphate and keratan sulphate, or a combination thereof.

46. A method according to any one of items 30-45, wherein the secondary graft polymers are chondroitin sulphate.

47. A method according to any one of items 30-46, wherein the secondary graft polymers have a molecular weight in the range of 10-1000 kDa.

48. A method according to any one of items 30-47, wherein the secondary graft polymers have a molecular weight in the range of 20-500 kDa.

49. A method according to any one of items 30-48, wherein the primary graft polymers are covalently grafted directly to the core polymer.

50. A method according to any one of items 30-49, wherein the primary graft polymers are covalently grafted to the core polymer through a linking group.

51. A method according to any one of items 30-50, wherein the secondary graft polymers are covalently grafted directly to the primary graft polymers.

52. A method according to any one of items 30-51, wherein the secondary graft polymers are covalently grafted to the primary graft polymers through a linking group.

53. A method according to any one of items 30-52, wherein the core polymer is a crosslinked hyaluronic acid, the primary graft polymers are dextran and the secondary graft polymers are chondroitin sulphate.
54. A method according to any one of items 30-53, wherein the pendant groups of the primary graft polymer in step b) are selected so as not to bind to the core polymer or other primary graft polymers under the conditions used in step d).
55. A method according to any one of items 30-54, wherein the pendant groups of the secondary graft polymer in step c) are selected so as not to bind to the core polymer, secondary graft polymer or other primary graft polymers under the conditions used in step e).
56. A method according to any one of items 30-55, wherein the pendant groups of the primary graft polymer in step b) are provided with protecting groups.
57. A method according to any one of items 30-56, wherein the pendant groups of the secondary graft polymer in step c) are provided with protecting groups.
58. A method according to any one of items 30-57, wherein the terminal group of the primary graft polymer in step b) is provided with a reactive linking group.
59. A method according to any one of items 30-58, wherein the terminal group of the secondary graft polymer in step c) is provided with a reactive linking group.

BRIEF DESCRIPTION OF THE DRAWINGS

FIG. 1 is a schematic illustration of an embodiment of a graft copolymer according to the present disclosure. The graft copolymer comprises two main substructures, wherein the first substructure consists of a crosslinked polysaccharide network (core polymer) and the second main substructure consists of multiple polysaccharide chains grafted onto a polymer chain, which in turn is grafted onto the first main substructure (secondary and primary grafts respectively)

EXAMPLES

Example 1a. Generation of the Core Polymer

The core polymer consists of hyaluronic acid (500-1000 kDa) that has been stabilized (crosslinked) with 1,4-butanediol diglycidyl ether, using methods previously described in WO9704012A1, followed by micronization to particle sizes of 0.01-5 mm and treating with sodium borohydride (0-25° C. during 0.5-2 hours) prior purification by precipitation and drying in vacuum, to obtain a crosslinking degree of 0.1-10% as determined by nuclear magnetic resonance spectroscopy using methods previously described (Edsman, K. et al. *Dermatol Surg* 38:1170-1179, 2012).

Example 1b. Synthesis of a Primary Graft

A primary graft has been prepared from dextran according to the following procedure.
1) Derivatization of the hydroxyl groups via a spacer by reacting dextran (100-500 kDa, 5-50 mg/mL) in an alkaline solution consisting of 0.1-2 M sodium hydroxide at pH 10-14, with 6-bromohexanoic acid (1-100 molar equivalents to dextran hydroxyl groups) at 15-95° C. for 2-24 hours followed by purification by precipitation in ethanol and drying in vacuum. The carboxylated dextran (5-50 mg/mL in aqueous solution) is subsequently converted to the corresponding protected hydrazide derivative (e.g. N-Boc) by activation of the carboxylic group, using 4-(4,6-dimethoxy-1,3,5-triazine-2-yl)-4-methylmorpholinium chloride (DMTMM) together with tert-butyl carbazate (1-100 molar equivalents of either reagent to introduced carboxylic groups on dextran during 1-120 hours at 0-50° C. and pH 4-10) followed by purification by precipitation in ethanol, drying in vacuum.
2) Derivatization of the reducing end of the modified dextran (5-50 mg/mL) by covalent addition of with a linker consisting of hexamethylene diamine (2-100 molar equivalents to reducing ends) in an aqueous solution containing sodium cyanoborohydride (2-100 molar equivalents to reducing ends) during 2-90 hours at 0-90° C. and pH 6-12 followed by precipitation in ethanol and drying in vacuum and characterization by nuclear magnetic resonance spectroscopy.

Example 1c. Conjugation of the Primary Graft to the Core Polymer

The modified polymer (primary graft) obtained in Example 1 b is covalently linked to the core polymer of Example 1a via an amidation reaction between the primary amines on the linker (located on the reducing end of the primary graft) and a carboxyl groups of the core polymer by treating an aqueous mixture of the core polymer (5-25 mg/mL) and the primary graft (5-25 mg/mL) with DMTMM (1-100 molar equivalents to primary amines) during 1-120 hours at 0-70° C. and pH 4-10. After purification by washing with excess deionized water and filtration, the N-Boc groups of the spacers on the primary grafts are removed by treating with diluted acid (0.2-4 M HCl or trifluoroacetic acid) during 1-120 hours at 0-70° C. and pH 1-6.

Example 1d. Conjugation of the Secondary Graft to the Primary Graft

In the final stage, secondary grafts are linked by reducing ends to free hydrazide groups on the primary grafts by mixing the dextran-grafted core polymer (5-25 mg/mL) with chondroitin sulfate (10-100 kDa, 1-100 molar equivalents with regard to reducing ends towards hydrazide groups) in an aqueous solvent containing sodium cyanoborohydride (2-100 molar equivalents to reducing ends) during 2-90 hours at 0-50° C. and pH 6-10, followed by precipitation in ethanol and drying in vacuum. The final product obtained is verified by determining the ratio between the polymers that compose the core polymer and the respective grafts using nuclear magnetic resonance (NMR) spectroscopy. The product obtained has a molecular structure as schematically illustrated in FIG. 1.

Example 2. Alternative Synthesis Route

Following the preparation of a core polymer as described in example 1a, an alternative route to synthesis of a primary graft involves direct derivatization of the reducing end of Dextran (1-100 kDa) as described in step 2) of example 1b, without modification of hydroxyl groups on the Dextran back-bone. The resulting Dextran derivative is further conjugated to the core polymer as described in example 1c.

The resulting product is subjected to mild oxidation using sodium periodate (≤1 molar equivalents to Dextran monosaccharide units) in aqueous media yielding aldehyde functionalities exclusively on the back-bone of the primary graft. A secondary graft polymer is prepared by derivatizing the reducing end of chondroitin sulfate (5-200 kDa, 40 mg/mL) with an excess of hexamethylene diamine dihydrochloride (15 mg/mL) in the presence of sodium cyanoborohydride (2-100 molar equivalents to reducing ends) in borate buffer at pH 10, followed by purification by dialysis (3.5 kDa molecular weight cutoff) and lyophilization.

The final product is then prepared by mixing an excess of the secondary graft (20-40 mg/mL) with the Dextran-grafted HA-gel particles (5-25 mg/mL) and sodium cyanoborohydride (1-50 molar equivalents) in aqueous media (room temperature, 16-24 h). Purification is carried out by extensive washing using sodium chloride (0.1-0.5 M) followed by precipitation and simultaneous washing in 70% ethanol and drying in vacuum.

The invention claimed is:

1. A graft copolymer comprising:
   (a) a core polymer comprising a crosslinked hyaluronic acid, and
   b) a plurality of dextran polymers covalently grafted to the core polymer; wherein the plurality of dextran polymers consist of a plurality of chondroitin sulphate polymers grafted to each dextran polymer.

2. The graft copolymer according to claim 1, wherein the core polymer has a molecular weight in the range of 50-5000 kDa.

3. The graft copolymer according to claim 1, wherein the core polymer comprises a polysaccharide gel.

4. The graft copolymer according to claim 1, wherein the dextran polymers comprise a water soluble polymer.

5. The graft copolymer according to claim 1, wherein the dextran polymers have a molecular weight in the range of 1-1000 kDa.

6. The graft copolymer according to claim 1, wherein the chondroitin sulphate polymers have a molecular weight in the range of 10-1000 kDa.

7. The graft copolymer according to claim 1, wherein the dextran polymers are covalently grafted, directly or through a linking group, to the core polymer by single end-point attachment.

8. The graft copolymer according to claim 1, wherein the chondroitin sulphate polymers are covalently grafted, directly or through a linking group, to the primary graft dextran polymers by single end-point attachment.

9. An injectable dermal aesthetic formulation comprising the graft copolymer according to claim 1.

10. The graft copolymer according to claim 2, wherein the core polymer has a molecular weight in the range of 100-1000 kDa.

11. The graft copolymer according to claim 6, wherein the chondroitin sulphate polymers have a molecular weight in the range of 20-500 kDa.

12. A method of preparing a graft copolymer, comprising:
   a) providing a core polymer comprising a crosslinked or non-crosslinked polysaccharide comprising a plurality of pendant functional groups,
   b) providing a primary graft polymer comprising a terminal functional group and a plurality of pendant functional groups,
   c) providing a secondary graft polymer comprising a terminal functional group,
   d) mixing the core polymer with the primary graft polymer under conditions allowing covalent binding of the primary graft polymer exclusively to the pendant functional groups of the core polymer via the terminal functional group of the primary graft polymer,
   e) mixing the grafted product of step d) with the secondary graft polymer under conditions allowing covalent binding of the secondary graft polymer exclusively to the pendant functional groups of the primary graft polymer via the terminal functional group of the secondary graft polymer,
   wherein the core polymer is a crosslinked hyaluronic acid, the primary graft polymer is dextran and the secondary graft polymer is chondroitin sulphate.

* * * * *